(12) United States Patent
Choi et al.

(10) Patent No.: US 11,191,787 B2
(45) Date of Patent: Dec. 7, 2021

(54) COMPOSITION FOR TREATING INFLAMMATORY DISEASE INDUCED BY HYPERIMMUNE RESPONSE

(71) Applicants: KOLON LIFE SCIENCE, INC., Seoul (KR); TISSUEGENE, INC., Rockville, MD (US)

(72) Inventors: Heonsik Choi, Seoul (KR); Kyoungbaek Choi, Incheon (KR); Hyeonyoul Lee, Gyeonggi-do (KR); Daewook Kim, Gyeonggi-do (KR); Hyesun Lee, Seoul (KR); Min Kim, Seoul (KR); Sujeong Kim, Seoul (KR)

(73) Assignees: KOLON LIFE SCIENCE, INC., Seoul (KR); KOLON TISSUEGENE, INC.

( * ) Notice: Subject to any disclaimer, the term of this patent is extended or adjusted under 35 U.S.C. 154(b) by 2 days.

(21) Appl. No.: 15/547,566

(22) PCT Filed: Feb. 5, 2016

(86) PCT No.: PCT/KR2016/001310
§ 371 (c)(1),
(2) Date: Jul. 31, 2017

(87) PCT Pub. No.: WO2016/126139
PCT Pub. Date: Aug. 11, 2016

(65) Prior Publication Data
US 2018/0264045 A1 Sep. 20, 2018

Related U.S. Application Data

(60) Provisional application No. 62/112,718, filed on Feb. 6, 2015.

(51) Int. Cl.
| A61K 35/32 | (2015.01) |
| A61P 29/00 | (2006.01) |
| A61K 35/12 | (2015.01) |
| A61P 3/10 | (2006.01) |
| A61P 19/02 | (2006.01) |
| A61K 38/18 | (2006.01) |
| A61K 48/00 | (2006.01) |

(52) U.S. Cl.
CPC .............. *A61K 35/32* (2013.01); *A61K 35/12* (2013.01); *A61K 38/1841* (2013.01); *A61P 3/10* (2018.01); *A61P 19/02* (2018.01); *A61P 29/00* (2018.01); *A61K 48/00* (2013.01)

(58) Field of Classification Search
CPC .... A61K 35/32; A61K 35/12; A61K 38/1841; A61K 48/00; A61P 3/10; A61P 19/02; A61P 29/00; Y10S 514/825
See application file for complete search history.

(56) References Cited

U.S. PATENT DOCUMENTS

| 6,413,511 | B1 | 7/2002 | Glorioso et al. | |
| 7,005,127 | B2 | 2/2006 | Song et al. | |
| 7,282,200 | B2 | 10/2007 | Song et al. | |
| 2003/0175257 | A1 | 9/2003 | Song et al. | |
| 2006/0115463 | A1* | 6/2006 | Song | A61K 35/32 424/93.21 |
| 2008/0233195 | A1* | 9/2008 | Spoom | A61K 31/26 424/486 |
| 2012/0201791 | A1* | 8/2012 | Yoo | A61K 35/28 424/93.7 |
| 2012/0207725 | A1* | 8/2012 | Cho | C07K 14/495 424/93.21 |

FOREIGN PATENT DOCUMENTS

| CN | 1653179 A | 8/2005 |
| CN | 1653179 A | 8/2005 |
| JP | 2005519698 A | 7/2005 |
| KR | 2009-0069013 A | 6/2009 |
| KR | 20090069013 A | 6/2009 |
| WO | 2011047345 A2 | 4/2011 |
| WO | 2011049291 A2 | 4/2011 |

OTHER PUBLICATIONS

Moskalewski et al. "Bone formation following intrarenal transplantation of isolated murine chondrocytes: chondrocyte-bone cell transdifferentiation?" Development 1989 107: 473-480. (Year: 1989).*
Bari et al. "Failure of in vitro-differentiated mesenchymal stem cells from the synovial membrane to form ectopic stable cartilage in vivo." Arthritis Rheum. Jan. 2004;50(1):142-50. (Year: 2004).*
Hu et al. "Cartilage to bone transformation during fracture healing is coordinated by the invading vasculature and induction of the core pluripotency genes." Development 2017 144: 221-234. (Year: 2017).*
Fox et al. "The Basic Science of Articular Cartilage Structure, Composition, and Function." Sports Health. Nov. 2009; 1(6): 461-468. (Year: 2009).*
Abramson Lab. "Stem Cells." retrieved from https://med.nyu.edu/medicine/labs/abramsonlab/stem-cells.html on Apr. 22, 2019. (Year: 2019).*
Kim et al. "Autologous chondrocyte implantation for rheumatoid arthritis of the knee: a case report." J Med Case Reports. 2009; 3: 6619. (Year: 2009).*

(Continued)

*Primary Examiner* — Titilayo Moloye
(74) *Attorney, Agent, or Firm* — The PL Law Group, PLLC

(57) ABSTRACT

Provided is a cell therapeutic agent for treating an inflammatory disease induced by a hyperimmune response, more specifically, a composition for treating an inflammatory disease induced by a hyperimmune response, which comprises (i) a chondrocyte or a cell capable of differentiating into a chondrocyte; and (ii) a cell into which a gene encoding TGF-β is introduced, wherein the cell in (ii) is derived from human embryonic kidney 293 (HEK-293) cell.

4 Claims, 11 Drawing Sheets
(5 of 11 Drawing Sheet(s) Filed in Color)
Specification includes a Sequence Listing.

(56) References Cited

OTHER PUBLICATIONS

Iannone et al. "Interleukin-10 and interleukin-10 receptor in human osteoarthritic and healthy chondrocytes." Clin Exp Rheumatol. Mar.-Apr. 2001;19(2): 139-45. (Year: 2001).*

Prekasan et al. "Review of the Tribological Characteristics of Synovial Fluid." Procedia Technology, vol. 25, 2016,pp. 1170-1174, ISSN 2212-0173, (Year: 2016).*

Akira, S., et al., "Interleukin-6 in Biology and Medicine", "Advances in Immunology", 1993, pp. 1-78, vol. 54.

Durante, W., et al., "Transforming Growth Factor-b1 Stimulates L-Arginine Transport and Metabolism in Vascular Smooth Muscle Cells: Role in Polyamine and Collagen Synthesis", "Circulation", Feb. 27, 2001, pp. 1121-1127, vol. 103.

Gonzalez-Rey, E., et al., "Human adipose-derived mesenchymal stem cells reduce inflammatory and T cell responses and induce regulatory T cells in vitro in rheumatoid arthritis", "Annals of the Rheumatic Diseases", Jan. 5, 2009, pp. 241-248, vol. 69.

Ha, C.-W., et al., "Initial phase I safety of retrovirally transduced human chondrocytes expressing transforming growth factor-beta-1 in degenerative arthritis patients", "Cytotherapy", 2012, pp. 247-256, vol. 14.

Hirano, T., et al., "Excessive production of interleukin 6/B cell stimulatory factor-2 in rheumatoid arthritis", "European Journal of Immunology", 1988, pp. 1797-1801, vol. 18.

Houssiau, F. A., et al., "Interleukin-6 in Synovial Fluid and Serum of Patients With Rheumatoid Arthritis and Other Inflammatory Arthritides", "Arthritis and Rheumatism", Jun. 1988, pp. 784-788, vol. 31, No. 6.

Hueber, W., et al., "Effects of AIN457, a Fully Human Antibody to Interieukin-17A, on Psoriasis, Rheumatoid Arthritis, and Uveitis", "Science Translational Medicine", Oct. 6, 2010, pp. 1-9; 52ra72, vol. 2, No. 52.

Kim, S. H., et al., "Effective Treatment of Established Murine Collagen-Induced Arthritis by Systemic Administration of Dendritic Cells Genetically Modified to Express IL-4", "The Journal of Immunology", 2001, pp. 3499-3505, vol. 166.

Kobayashi, K., et al., "Sodium Iodoacetate-Induced Experimental Osteoarthritis and Associated Pain Model in Rats", "The Journal of Veterinary Medical Science", Dec. 2003, pp. 1195-1199, vol. 65, No. 11.

Lafyatis, R., et al., "Transforming growth factor-beta production by synovial tissues from rheumatoid patients and streptococcal cell wall arthritic rats: Studies on secretion by synovial fibroblast-like cells and immunohistologic localization", "The Journal of Immunology", Aug. 15, 1989, pp. 1142-1148, vol. 143, No. 4.

Lee, K. H., et al., "Regeneration of Hyaline Cartilage by Cell-Mediated Gene Therapy Using Transforming Growth Factor b1-Producing Fibroblasts", "Human Gene Therapy", Sep. 20, 2001, pp. 1805-1813, vol. 12.

Leisten, J. C., et al., "Interleukin-6 Serum Levels Correlate with Footpad Swelling in Adjuvant-Induced Arthritic Lewis Rats Treated with Cyclosporin A or Indomethacin", "Clinical Immunology and Immunopathology", 1990, pp. 108-115, vol. 56.

Melnyk, V. O., et al., "Synoviocytes Synthesize, Bind, and Respond to Basic Fibroblast Growth Factor", "Arthritis and Rheumatism", Apr. 1990, pp. 493-500, vol. 33, No. 4.

Nouri, A. M. E., et al., "Cytokines and the chronic inflammation of rheumatic disease. I. The presence of interleukin-1 in synovial fluids", "Clinical & Experimental Immunology", 1984, pp. 295-302, vol. 55.

Saxne, T., et al., "Detection of Tumor Necrosis Factor a but Not Tumor Necrosis Factor b in Rheumatoid Arthritis Synovial Fluid and Serum", "Arthritis and Rheumatism", Aug. 1988, pp. 1041-1045, vol. 31, No. 8.

Seitz, M., et al., "Enhanced Production of Neutrophil-activating Peptide-1/Interleukin-8 in Rheumatoid Arthritis", "Journal of Clinical Investigation", Feb. 1991, pp. 463-469, vol. 87.

Song, S. U., et al., "Hyaline Cartilage Regeneration Using Mixed Human Chondrocytes and Transforming Growth Factor-b1-Producing Chondrocytes", "Tissue Engineering", 2005, pp. 1516-1526, vol. 11, No. 9/10.

Takai, Y., et al., "Enhanced Production of Interleukin-6 in Mice with Type II Collagen-Induced Arthritis", "Arthritis and Rheumatism", May 1989, pp. 594-600, vol. 32, No. 5.

Thornton, S. C., et al., "Identification of the major fibroblast growth factors released spontaneously in inflammatory arthritis as platelet derived growth factor and tumour necrosis factor-alpha", "Clinical & Experimental Immunology", 1991, pp. 79-86, vol. 86.

Wang, L., et al., "Human Umbilical Cord Mesenchymal Stem Cell Therapy for Patients with Active Rheumatoid Arthritis: Safety and Efficacy", "Stem Cells and Development", Aug. 13, 2013, pp. 3192-3202, vol. 22, No. 24.

Note: For the non-patent literature citations that no month of publication is indicated, the year of publication is more than 1 year prior to the effective filing date of the present application.

Chucchiarini, M., et al., "The potential of gene transfer for the treatment of osteoarthritis", "Regenerative Medicine", 2014, pp. 5-8, vol. 9, No. 1, Publisher: XP055497085, GB.

Chang, W., et al., "Therapeutic Potential of Autologous Mesenchymal Stem Cells Derived From Synovial Fluid in Patients With Degenerative Arthritis", "Animal Cells and Systems", 2013, pp. 315-324, vol. 17, No. 5.

Evans, C., et al., "Arthritis Gene Therapy and Its Tortuous Path Into the Clinic", "Transl Res.", Apr. 2013, pp. 205-216, vol. 161, No. 4.

Noh, M., et al., "Pre-Clinical Studies of Retrovirally Transduced Human Chondrocytes Expressing Transforming Growth Factor-Beta-1 (TG-C)", "Cytotherapy", 2010, pp. 384-393, vol. 12.

Zheng, Z., et al., "Allogenic Mesenchymal Stem Cell and Mesenchymal Stem Cell-Differentiated Chondrocyte Suppress the Responses of Type II Collagen-Reactive T Cells in Rheumatoid Arthritis", "Rheumatology", 2008, pp. 22-30, vol. 47.

Igaku-Shoin, "A Medicine Great Dictionary; 1st edition 1st printing", 2003, p. 2245, "degenerative arthritis", Eng Translation.

Igaku-Shoin, "A Medicine Great Dictionary; 1st edition printing", 2003, p. 2245, "degenerative arthritis".

* cited by examiner

FIG. 5

|  | Negative control | Type I Collagen | Type II Collagen |
|---|---|---|---|
| Untreated |  |  |  |
| Control |  |  |  |
| hChonJ |  |  |  |
| hChonJb#7 |  |  |  |
| Mixed cells |  |  |  |

```
                      SEQUENCE LISTING

<160> NUMBER OF SEQ ID NOS: 22

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
tgctggttgg tcttttcca                                                    19

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
tgactgctct tcagaacaaa                                                   20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
tcctccagca gtgggaaaca                                                   20

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
tttgtaggtt tcgggtatcc ttgc                                              24

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
ctcagcgtct ctgctgtcac                                                   20

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
```

```
ggccagtctc agttccttct t                                              21
```

```
<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ttgatgttga tggactggac                                                20

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
tctctggctt atgattacct tc                                             22

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tccaggatga ggacccaagc                                                20

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
tcgtcatcat cccacgagtc a                                              21

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
actgaacttc ggggtgattg                                                20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gcttggtggt ttgctacgac                                                20

<210> SEQ ID NO 13
<211> LENGTH: 20
<212> TYPE: DNA
<213> ORGANISM: Artificial Sequence
```

```
<220> FEATURE:
<223> OTHER INFORMATION: primer

<400> SEQUENCE: 13
caaggcagtg gagcaggtga                                                      20

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
ccgggtggtt caatttttca tt                                                   22

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
agagtttccg cctccaacca                                                      20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
cgggactggg ctagttcagg                                                      20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ctggtcaccc tgccattgat                                                      20

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
aggcatggcc aaaatacaaa gaaac                                                25

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
actggggctc ttggaaacta cac                                                  23
```

-continued

```
<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
ccttggtttt gttcgggttc a                                              21

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
agttcgccat ggatgacgat                                                20

<210> SEQ ID NO 22
<211> LENGTH: 17
<212> TYPE: DNA
<213> ORGANISM: Artificial Sequence
<220> FEATURE:
<223> OTHER INFORMATION: primer

<400> SEQUENCE: 22
aagccggcct tgcacat                                                   17
```

COMPOSITION FOR TREATING INFLAMMATORY DISEASE INDUCED BY HYPERIMMUNE RESPONSE

CROSS-REFERENCE TO RELATED APPLICATIONS

This application is a U.S. national phase under the provisions of 35 U.S.C. § 371 of International Patent Application No. PCT/KR2016/001310 filed Feb. 5, 2016, which in turn claims priority of U.S. Provisional Patent Application No. 62/112,718 filed Feb. 6, 2015. The disclosure of such international patent application and U.S. priority patent application are hereby incorporated herein by reference in their respective entireties, for all purposes.

TECHNICAL FIELD

The present invention relates to a cell therapeutic agent, more specifically, it relates to a cell therapeutic agent for treating an inflammatory disease induced by a hyperimmune response, which comprises (i) a chondrocyte or a cell capable of differentiating into a chondrocyte; and (ii) a cell into which a gene encoding TGF-β (transforming growth factor-beta) is introduced, wherein the cell in (ii) is hChonJb#7.

DESCRIPTION OF THE RELATED ART

Degenerative arthritis is a disease caused by gradual loss of cartilage which protects the joints due to aging, and it is apt to occur in the knee joint which supports a significant portion of the body weight.

In contrast, rheumatoid arthritis of an autoimmune disease is a disease that our body's immune cells attack the joints to cause inflammation and inflammation of the joints continuously infiltrates into the articular cartilage and bone tissue, resulting in tissue erosion. Rheumatoid arthritis often occurs in fingers and wrists, and it is especially characterized by protruded middle nodes of the fingers. Unlike degenerative arthritis, which occurs mainly at the age of fifties or elder, rheumatoid arthritis often occurs at young ages.

The causes, symptoms, sites of onset, and ages of onset of degenerative arthritis and rheumatoid arthritis are compared to each other as follows (Table 1).

TABLE 1

|  | Degenerative arthritis | Rheumatoid Arthritis |
| --- | --- | --- |
| Cause | Aging, overweight, repetition of severe motion | Immune dysfunction |
| Symptom | Unnatural walking, Pain after movement | Pain and flash at the joint site, Pain after break |
| Region | Large joints such as knees, hips, hip joints | Small joints such as fingers, wrists, and toe fingers |
| Age | Elderly people after 50s | All ages |

It has been reported that when rheumatoid arthritis occurs, the production of cytokines increases in joint macrophages or fibroblasts and the production of IFN-γ by Th1 cells and IL-17 cytokine by Th17 cells increases. Although cytokines produced in Th1 and Th17 cells exacerbate the arthritic symptoms, cytokines produced by Th2 cells such as IL-4 and IL-10 are known to prevent or treat arthritis. It has been reported that when a viral vector including IL-4 or IL-10 gene of a Th2 type cytokine is injected into a joint of an arthritis-induced mouse, the therapeutic effect is exerted not only at the injected leg but also at the other legs (S H Kim et al., J. Immunol., 166: 3499-3505 (2001)).

Small molecules that have been developed so far as therapeutic agents or reducing agents for rheumatoid arthritis include methotrexate, azathioprine, cyclophosphamide, and corticosteroids, and also Enbrel (ingredient name: etanercept), and Remicade (ingredient name: infliximab), Humira (ingredient name: adalimimab) of TNF-α antagonists as biological agents. Most of the therapeutic agents which have been so far developed for rheumatoid arthritis have adverse effects such as gastrointestinal disorders, and cannot significantly suppress the progress of joint damage.

TGF-β1, one of the cell therapeutic agent components of the present invention, is a multifunctional modulator for cell growth and differentiation. It has been reported that the neuropathic pain due to nerve injury is significantly reduced by intrathecal injection of recombinant TGF-β1 by targeting various types of cells with multi-differentiating potencies.

It has been recently reported that chondrocytes expressing TGF-β1 or fibroblasts are effective in treating degenerative arthritis (Lee K H et al., Hum Gene Ther 2001; 12: 1805-1813, SUN U. SONG et al. Tissue Engineering 2005, 11:1516-1526), but the possibility of treating rheumatoid arthritis which has different causes and pathologies from those of degenerative arthritis has not been reported.

Accordingly, the present inventors have made efforts to develop a cell therapeutic agent having anti-inflammatory action and therapeutic effect for rheumatoid arthritis, and as a result, it has been confirmed that the symptoms of rheumatism are improved when a mixed cell composition of a chondrocyte and a cell expressing TGF-β1 is treated to a rheumatoid arthritis-induced animal model, whereby the present invention has been completed.

SUMMARY

An object of the present invention is to provide a therapeutic use of a chondrocyte or a cell capable of differentiating into a chondrocyte and a cell expressing TGF-β1, which is not a chemically synthesized drug, for treating an inflammatory disease induced by a hyperimmune response, wherein the cell in (ii) is hChonJb#7.

In order to accomplish the above object, an aspect of the present invention provides a composition for treating an inflammatory disease induced by a hyperimmune response, which comprises (i) a chondrocyte or a cell capable of differentiating into a chondrocyte, and (ii) a cell into which a gene encoding TGF-β is introduced, wherein the cell in (ii) is hChonJb#7.

Another aspect of the present invention provides a method of treating an inflammatory disease induced by a hyperimmune response, which comprises administering to a subject with a composition comprising (i) a chondrocyte or a cell capable of differentiating into a chondrocyte; and (ii) a cell into which a gene encoding TGF-β is introduced, wherein the cell in (ii) is hChonJb#7.

Further, still another aspect of the present invention provides a use of a composition comprising (i) a chondrocyte or a cell capable of differentiating into a chondrocyte; and (ii) a chondrocyte into which a gene encoding TGF-β is introduced as a therapeutic agent for treating an inflammatory disease induced by a hyperimmune response, wherein the cell in (ii) is hChonJb#7.

Yet still another aspect of the present invention provides a method of inhibiting the expression or activity of a cytokine selected from the group consisting of IL-6, IL-17A, IL-1β, and TNF-α, which comprises administering to a subject with a composition comprising (i) a chondrocyte or a cell capable of differentiating into a chondrocyte; and (ii) a cell into which a gene encoding TGF-β is introduced, wherein the cell in (ii) is hChonJb#7.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other aspects, features and other advantages of the present disclosure will be more clearly understood from the following detailed description taken in conjunction with the accompanying drawings, in which.

FIG. 5 illustrates the results for immunostaining performed to confirm the content of type 1 collagen and type 2 collagen in the cartilage after treatment of a mixed cell to an animal model suffering with degenerative arthritis.

DETAILED DESCRIPTION OF THE PREFERRED EMBODIMENT

Figure 1:
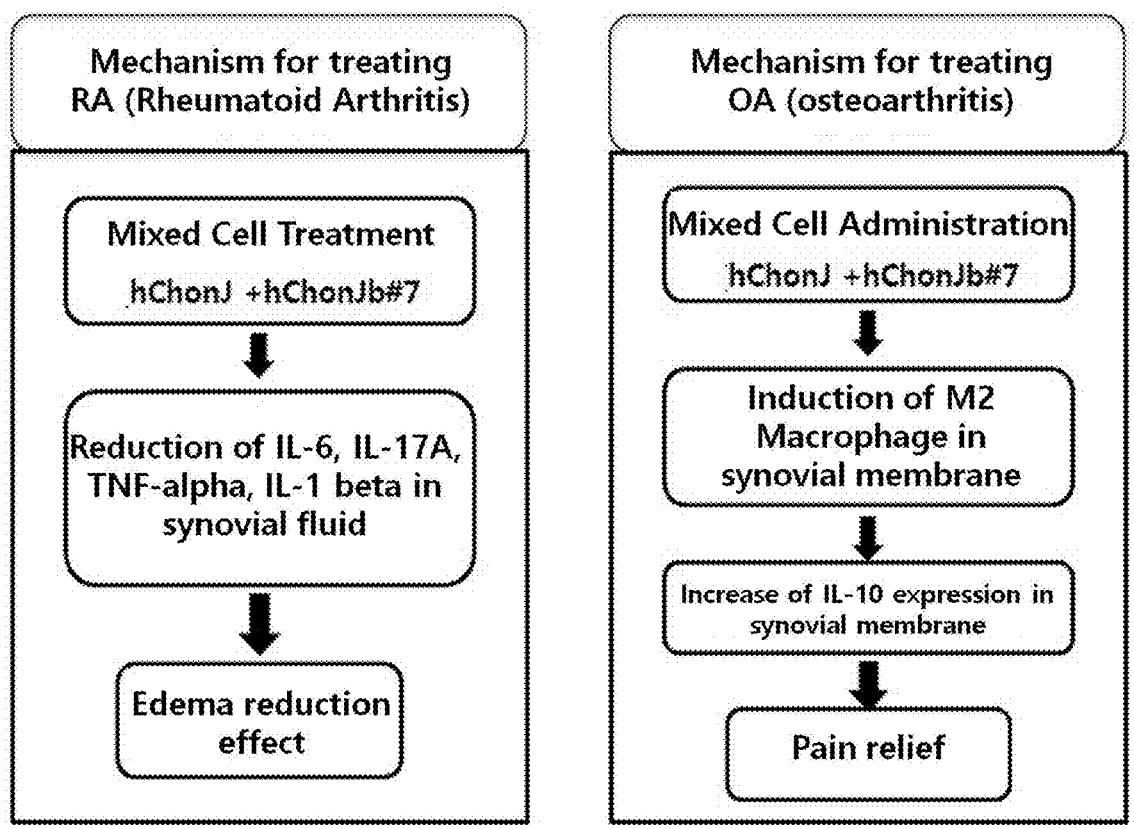
FIG. 1 is a diagram illustrating the mechanism of a therapeutic action of a mixed cell composition of the present invention for rheumatoid arthritis and degenerative arthritis.

A mixed cell comprising an allogeneic (non-autologous) chondrocyte; and hChonJb#7 expressing TGF-β is known as a cell-mediated gene therapeutic agent for degenerative arthritis. In a phase 2 clinical study for patients suffering with osteoarthritis, it has been confirmed that the mixed cell improves pain, activity and cartilage structures of patients suffering with osteoarthritis. However, a mechanism by which the mixed cell acts is not yet found.

The present inventors observed effects on pain and structural transformation after injection of the mixed cell to an osteoarthritis-induced animal model and confirmed whether the mixed cell induces an anti-inflammatory environment, and as a result, it has been confirmed that anti-inflammatory cytokines and M2 macrophages are increased in the arthritic knee joint treated with mixed cell to induce an anti-inflammatory environment that alleviates pain and induces joint regeneration.

Accordingly, it has been confirmed that the mixed cell induces an M2 macrophage-rich environment with immunosuppressive properties, and under the assumption that the mixed cell has an effect even on an inflammatory disease induced by a hyperimmune response, in a rheumatoid arthritis animal model, a chondrocyte and hChonJb#7 are mixed at a predetermined ratio and treated to knee joints. As a result, in a group treated with the mixed cell, it was confirmed that the metatarsal edema was reduced and further, it was confirmed that expression of IL-6, IL-17A, IL-1β, and TNF-α as cytokines that induced and promoted an inflammatory response in the synovial lavage fluid was reduced. A therapeutic effect by a single dose of the mixed cell lasted for 26 days.

Conventionally, materials such as methotrexate (MTX) used as a therapeutic agent for rheumatoid arthritis may cause digestive system and mouth ulcers and are at risk for causing hepatotoxicity, renal failure, and the like. Further, therapeutic agents such as anti-TNF-α antibodies comprising Remicade and the like are known to disturb a patient's innate immune system, resulting in the expression of tuberculosis (TB) from a tuberculosis carrier. In contrast, a cell therapeutic agent according to the present invention has an advantage in that the above adverse effects are not shown in a clinical test result for degenerative arthritis. Accordingly, the present inventors have confirmed the possibility that the mixed cell may be a novel therapeutic agent which overcomes disadvantages of conventional therapeutic agents for rheumatoid arthritis.

Therefore, an aspect of the present invention relates to a composition for treating an inflammatory disease induced by a hyperimmune response, which comprises (i) a chondrocyte or a cell capable of differentiating into a chondrocyte; and (ii) a cell into which a gene encoding TGF-β is introduced, wherein the cell in (ii) is hChonJb#7.

Another aspect of the present invention relates to a method of treating an inflammatory disease induced by a hyperimmune response, which comprises administering to a subject with a composition comprising (i) a chondrocyte or a cell capable of differentiating into a chondrocyte; and (ii) a cell into which a gene encoding TGF-$ is introduced, wherein the cell in (ii) is hChonJb#7.

Still another aspect of the present invention relates to a use of a composition comprising (i) a chondrocyte or a cell capable of differentiating into a chondrocyte; and (ii) a cell into which a gene encoding TGF-β is introduced as a therapeutic agent for treating an inflammatory disease induced by a hyperimmune response, wherein the cell in (ii) is hChonJb#7.

In the present invention, the inflammatory disease induced by the hyperimmune response comprises rheumatoid arthritis, multiple sclerosis, systemic lupus erythematosus, myasthenia gravis, colitis, type 1 diabetes, encephalitis, and the like, and among the diseases, it is particularly effective in the treatment for rheumatoid arthritis.

In the present invention, the cell capable of differentiating into the chondrocyte may be a cartilage precursor cell or a stem cell.

In the present invention, (i) the chondrocyte or the cell capable of differentiating into a chondrocyte and (ii) the cell into which a gene encoding TGF-β is introduced may be mixed at various mixing ratios, and the ratio of (i) and (ii) may be preferably 1:1 to 100:1 and more preferably 3:1, wherein the cell in (ii) is hChonJb#7.

In an aspect of the present invention, the composition for treating the inflammatory disease induced by the hyperimmune response comprises a non-transduced human chondrocyte (hChonJ cell) and a cell (hChonJb#7) expressing TGF-β1, more specifically, a human allogeneic chondrocyte (hChonJ) and a cell expressing human TGF-β1 The two types of cells may be mixed at various mixing ratios. For example, these two cells may be mixed at a ratio of 3:1, that is, a ratio at which the hChonJ cell is 3 and the hChonJb#7 is 1. The mixed cell at the ratio of 3:1 and a production method thereof are disclosed in a thesis [Cytotherapy, 2012 February, 14(2): 247-256] and U.S. Pat. Nos. 7,005,127 and 7,282,200.

In an aspect of the present invention, in an arthritis rat model treated with the mixed cell, the pain started to be reduced from 15 days after treatment and a pain relief effect was continued up to the time (an experiment end date) after 56 days after treatment. It has been confirmed that the pain relief was associated with a structural improvement of arthritic knee joints, and the treated mixed cell was found to be effective for both pain relief and cartilage regeneration. That is, the mixed cell used in the present invention is a cell-mediated gene therapy for pain relief and regeneration of cartilage tissue.

In another aspect of the present invention, with respect to the cartilage tissue in the arthritis rat model treated with the mixed cell, staining for type 1 collagen and type 2 collagen was performed and histologically analyzed, and as a result, it was confirmed that the mixed cell regenerated a hyaline cartilage tissue which was type 2 collagen-positive.

The macrophages which are innate immune cells are classified into activated "M1 macrophages" having a pro-inflammatory property and activated "M2 macrophages" having an immunosuppressive property according to an activation phenotype. IFN-γ is a key cytokine involved in the activation of the M1 macrophages and a TLR signal induced by pathogen recognition contributes to differentiation of the M1 macrophages. It has been known that the M1 macrophages increase expression of TNFα, IL-12 and IL-23 and decrease expression of IL-10 to induce Th1 and Th17 immune responses which cause tissue damage. In contrast, the M2 macrophages increase the expression level of IL-10 and decrease expression of IL-12, thereby reducing inflammation and promoting tissue regeneration.

Figure 8:
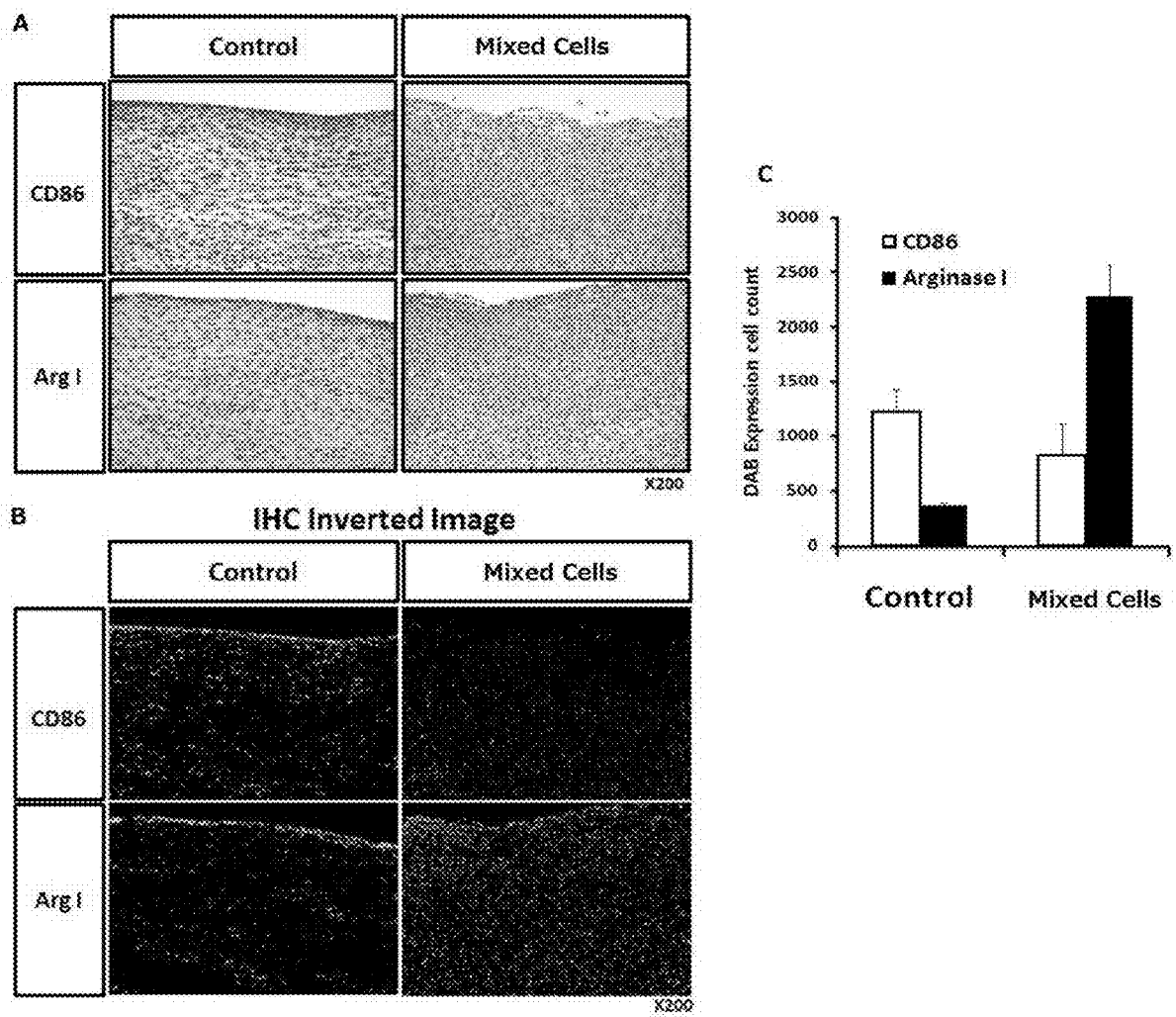
FIG. 8A illustrates the results for immunochemical staining of synovial membrane with antibodies to CD86 and arginase 1, 8B illustrates the image of 8A converted to an invert version by using Image-Pro Plus, and 8C is a graph illustrating CD86 and arginase 1 positive cells measurement.

In an aspect of the present invention, TGF-β1 expressed in the hChonJb#7 which is a cell expressing TGF-β1 and IL-10 induced through the hChonJ which is a human chondrocyte induces generation of the M2 macrophages and it is determined that the generated M2 macrophages secrete IL-10 to create an anti-inflammatory environment in the joints treated with the mixed cell. The synovial membrane in the animal model treated with the mixed cell are histologically analyzed, and as a result, it can be confirmed that the M2 macrophages are increased (FIGS. 8A through 8C).

Further, it is determined that an immunosuppressive effect of the composition of the present invention is induced by an increase in expression of TGF-β1 and arginase 1, and in an aspect of the present invention, in the keen joint synovial membrane in an animal model of a group treated with the mixed cell, the expression of arginase 1 is increased.

It is known that the increase in the expression of arginase 1 and a decrease in L-arginine thereby cause a strong immunosuppressive effect in an immune system and further, it has been reported that the TGF-β induces transcription of arginase 1 and activity of arginase (Durante et al., Circulation, 103(8), 1121-7, 2001). Accordingly, it is determined that the M2 macrophages may more efficiently regulate the immune in the present of TGF-β1.

Further, in the anti-inflammatory effect of the composition of the present invention, it is shown that IL-10 expressed in the M2 macrophage induced by treatment of the mixed cell activates STAT3 and PI3K and an anti-inflammatory effect is shown by Hmox-1 regulated thereby.

Meanwhile, recently, in the synovial membrane and the synovial fluid of a patient suffering with chronic rheumatoid arthritis, cytokines and growth factors, such as interleukin-1 (IL-1), interleukin-8 (IL-8), tumor necrosis factor-α (TNF-α), transforming growth factor β (TGF-β), fibroblast growth factor (FGF), and platelet-derived growth factor (PDGF) have been detected (Nouri et al., Clin. Exp. Immunol. 55: 275-372, 1984; Thornton et al., Clin. Exp. Immunol. 86: 79-86, 1991; Saxne, et al., Arthritis Rheum. 31:1041-1045, 1988; Seitz et al., J. Clin. Invest. 87: 463-469, 1991; Lafyatis et al., J. Immunol. 143: 1142-1148, 1989; Melnyk et al., Arthritis Rheum. 33: 493-500, 1990).

IL-6 is a cytokine known as B-cell stimulating factor 2 or interferon β2. IL-6 is a differentiation factor involved in activation of B lymphocytic cells (Hirano T. et al., Nature 324, 73-76, 1986) and is known as a multifunctional cytokine that affects an action of various types of cells (Akira, S. et al., Adv. In Immunology 54, 1-78, 1993).

It has been reported that in the serum or the synovial fluid of the patient suffering with the chronic rheumatoid arthritis, a large amount of interleukin-6 and soluble IL-6 receptors are present (Houssiau et al., Arthritis Rheum. 31: 784-788, 1988; Hirano et al., Eur. J. Immunol. 18: 1797-1801, 1988; Yoshioka et al., Japn. J. Rheumatol. In press). Even in the animal model of rheumatoid arthritis, a similar result is obtained (Takai et al., Arthritis Rheum. 32: 594-600, 1989, Leisten et al., Clin Immunol Immunopathol 56: 108-115, 1990), and as a result, the IL-6 is known as a factor associated with the chronic rheumatoid arthritis.

Meanwhile, in a clinical development for rheumatoid arthritis, secukinumab as a biological agent is a high-affinity human monoclonal antibody that inhibits IL-17A activity. In the RA proof-of-concept (PoC) study, secukinumab was co-treated to an active RA patient treated with a stable dose of MTX. As a result, it was confirmed that a treatment group using secukinumab rapidly improved clinical symptoms of rheumatoid arthritis compared to placebo (Hueber et al (2010) Sci. Transl. Med 2(52):52-72). This is data showing that neutralization of IL-17A may be efficacious in the patient suffering with rheumatoid arthritis.

In another aspect of the present invention, it was confirmed that the mixed cell was treated to the paw of a rat in which rheumatoid arthritis was induced by treatment of a complete Freund's adjuvant (CFA) and the metatarsal edema was confirmed for 28 days. As a result, in the group treated with the mixed cell, it was confirmed that the metatarsal edema was decreased (FIGS. 10A and 10B), and as the result of analyzing IFN-γ, IL-6, IL-17A, IL-1β, and TNF-α which were Pro-inflammatory cytokine items that induced and promoted the inflammatory response, it was confirmed that in the mixed cell-treated group and the MTX-treated group, the metatarsal edema was statistically and significantly decreased as compared with a control.

Therefore, the composition of the present invention has an effect of inhibiting expression of IL-6, IL-17A, IL-1β, and TNF-α which are inflammatory cytokines that are excessively secreted from the joint synovial lavage fluid of the patient suffering with rheumatoid arthritis to reduce the edema.

Hereinafter, the present invention will be described in more detail through Examples. These Examples are just to exemplify the present invention, and it is apparent to expert in the field that it is interpreted that the scope of the present invention is not limited to these Examples.

Example 1: Induction of Pain Relief and Regeneration of Col 11 Positive Cartilage by Treatment of Mixed Cell in Arthritis Animal Model In the case of treating a mixed cell in a clinical phase 2 for patients suffering with arthritis, it was observed that pain was reduced and an environment of joints was structurally improved. In order to confirm a mechanism therefor, in a degenerative arthritis animal model induced by MIA, a mixed cell was treated and a joint histological examination and a von Frey filament test were performed.

1-1: Preparation of MIA-Induced Arthritis Animal Model

In preparation of an animal model, a 6-week-old male rat (Spargue-Dawley, 200 to 225 g, Nara Biotech, Korea) were used. An animal experiment was conducted under a veterinary control after approval of the Kolon Life Science (Korea) Institutional Animal Care and Use Committee (IACUC No. KLS IACUC 2013-04).

In order to induce arthritis, 50 μl of an MIA (monosodium iodoacetate, Sigma, USA) solution having a concentration of 60 mg/mL was treated to the articular cavity of the left knee of a rat by using a 31 G syringe.

1-2. Preparation of Cells for Cell Therapy

The hChonJ used in the present invention is a human-derived chondrocyte. Preparation methods and mixing ratios of the cells are disclosed in a thesis [Cytotherapy, 2012 February; 14(2): 247-256] and U.S. Pat. Nos. 7,005,127 and 7,282,200.

The hChonJb#7 may be prepared by injecting a cDNA of TGF-β into cells according to a known method. For example, a promoter such as methallothionein and a cDNA of TGF-β are included in a known vector [for example, pUC19 (including an ampicillin resistance gene) by Gibco-BRL Corporation] having a resistance gene such as ampicillin and neomycin to prepare a vector including the cDNA of TGF-β. Thereafter, the vector including the cDNA of TGF-β is injected into a cell according to a known method such as a calcium phosphate method or a lipofectin method to prepare the hChonJb#7.

1-3: Confirmation of Pain Relief and Cartilage Regeneration Effects by Treatment of Mixed Cell After 2 weeks of MIA injection, mixed cells ((1.2×10$^6$ cells: hChonJ (9×10$^5$ cells)+hChonJb#7 (3.0×10$^5$ cells)), hChonJ (9×10$^5$ cells), hChonJb#7 (3.0×10$^5$ cells) or a control {CryoStor-10 (CS-10)} were treated to the articular cavity of the left knee. General symptoms were observed, and body weights were measured once a week.

Figure 2:
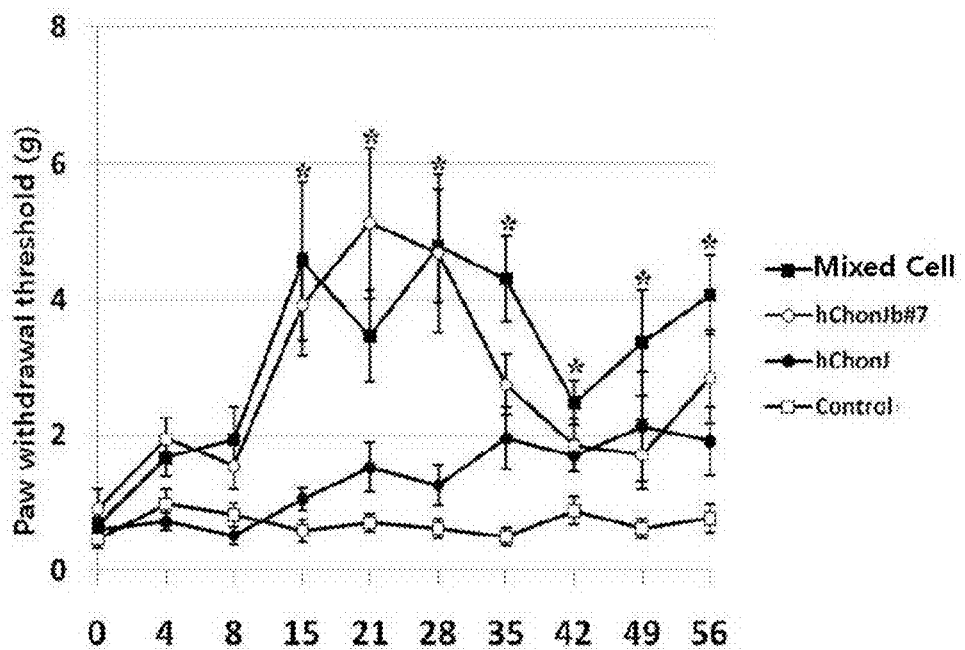
FIG. 2 illustrates the results for the pain relief effect after treatment of a mixed cell to an animal model suffering with degenerative arthritis confirmed through the von Frey filament test.

The pain relief was observed by performing a von Frey filament test, and as a result, as illustrated in FIG. 2, pain levels decreased from 15 days after cell treatment, and such effects lasted until the end of observation (56th day after treatment) in the case of a group treated with hChonJb#7 (3.0×10$^5$ cells) expressing TGF-β, the pain relief was observed from 15 days, but after 6 weeks, it was confirmed that the effect disappeared. In contrast, in a group treated with hChonJ (9×10$^5$ cells) which was a normal human chondrocyte, the pain relief effect was not observed.

Figure 3:
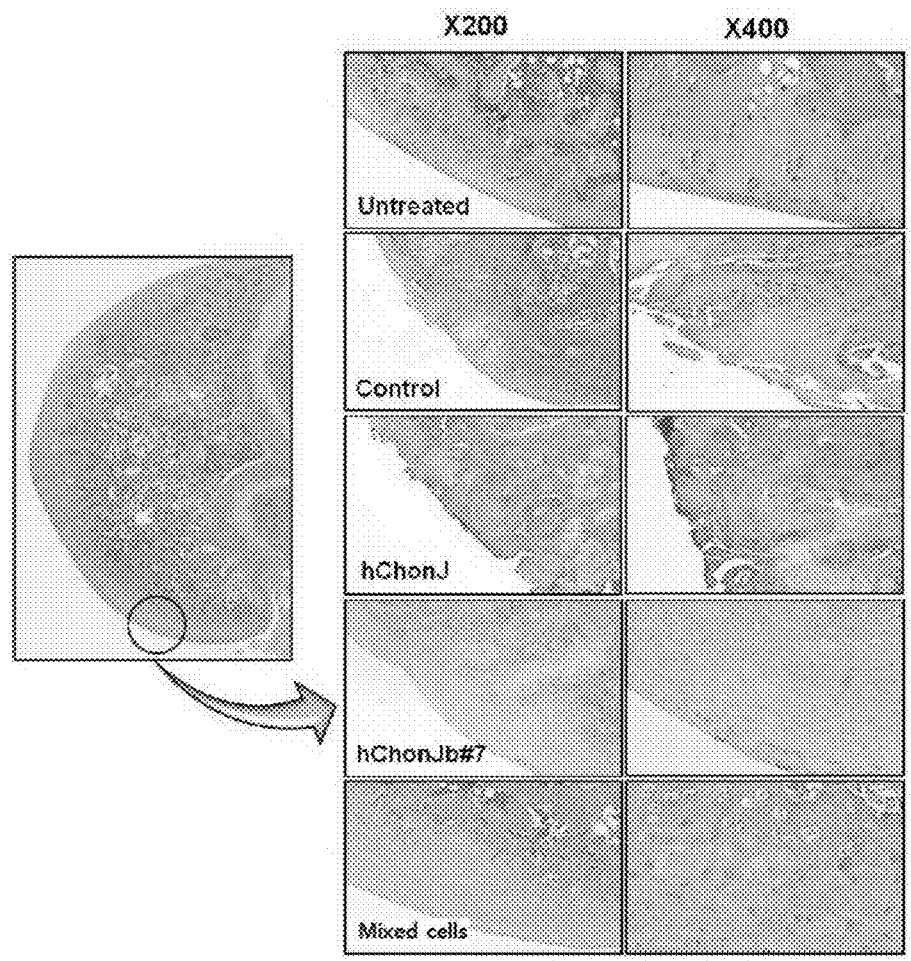
FIG. 3 illustrates the results for H&E staining performed to confirm the cartilage status of the knee joint after treatment of a mixed cell to an animal model suffering with degenerative arthritis.
Figure 4:
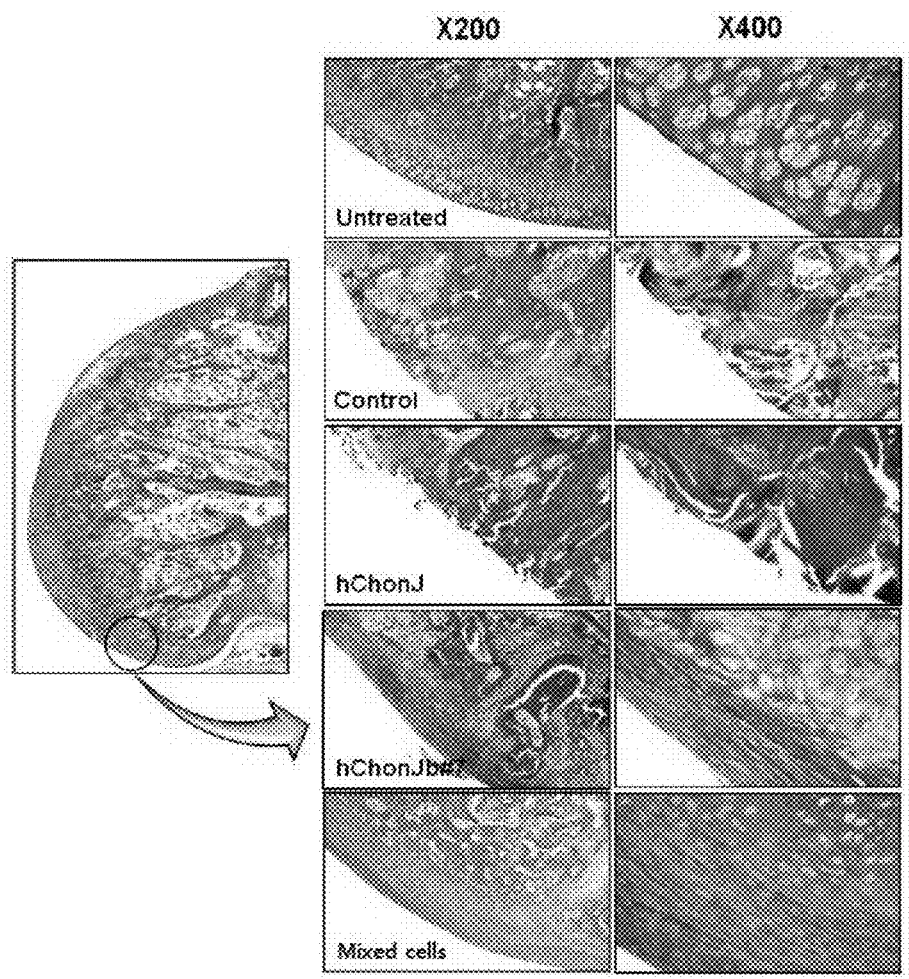
FIG. 4 illustrates the results for Masson's trichrome staining performed to confirm the cartilage status of the knee joint after treatment of a mixed cell to an animal model suffering with degenerative arthritis.

In order to confirm whether the pain relief effect of the mixed cell is associated with cartilage regeneration, left knee joints in 5 experimental groups were harvested and a histological analysis was performed through H&E staining and Masson's trichrome staining (see FIGS. 3 and 4).

In a control (CS-10) and an hChonJ-treated group, cartilage regeneration was not confirmed. In contrast, in an hChonJb#7-treated group and a mixed cell-treated group, more cartilage was observed than other controls.

Further, as the immunohistochemical staining result, as illustrated in FIG. 5, it was confirmed that the content of type II collagen in the cartilage in the mixed cell-treated group was higher than that in the hChonJb#7-treated group, and from the result, it can be seen that the cartilage in the mixed cell-treated group is close to the hyaline cartilage.

In order to evaluate the improvement degree of the joint status, as a method disclosed in the thesis [Kobayasi, K., J. et al., J. Vet. Med. Sci., 65:1195-1199, 2003], the histopathological results and the pathology scores of the H&E-stained joint tissue were evaluated and the results were summarized in the following Table 2. In the experimental results below, the cartilage in the mixed cell-treated group was most improved

TABLE 2

| Treatment | No. of Animals | Untreated 5 (×3) | Control 6 (×3) | hChonJ 6 (×3) | hChonJb#7 6 (×3) | Invossa 6 (×3) |
|---|---|---|---|---|---|---|
| Structural change in the joint | 1 | 2/15 | 3/18 | 0/18 | 5/18 | 7/18 |
| Surface irregularities | 2 | 0/15 | 4/18 | 1/18 | 2/18 | 4/18 |
|  | 3 | 0/15 | 10/18 | 14/18 | 6/18 | 4/18 |
| Average pathology score |  | 0.13 | 2.28 | 2.44 | 1.50 | 1.50 |
| Standard Error |  | 0.09 | 0.23 | 0.22 | 0.29 | 0.25 |
| Ulceration | 1 | 1/15 | 3/18 | 3/18 | 8/18 | 7/18 |
|  | 2 | 0/15 | 8/18 | 7/18 | 6/18 | 6/18 |
|  | 3 | 0/15 | 7/18 | 7/18 | 3/18 | 0/18 |
| Average pathology score |  | 0.07 | 2 22 | 2.11 | 1.61 | 1.06 |
| Standard Error |  | 0.07 | 0.18 | 0.18 | 0.21 | 0.19 |
| Fibrillation of cartilage surface | 1 | 0/15 | 3/18 | 3/18 | 1/18 | 3/18 |
|  | 2 | 0/15 | 2/18 | 6/18 | 6/18 | 5/18 |
|  | 3 | 0/15 | 7/18 | 5/18 | 6/18 | 1/18 |
| Average pathology score |  | 0 | 1.56 | 1.67 | 1.72 | 0.89 |
| Standard Error |  | 0 | 0.32 | 0.26 | 0.29 | 0.25 |

TABLE 2-continued

| Treatment | No. of Animals | Untreated 5 (×3) | Control 6 (×3) | hChonJ 6 (×3) | hChonJb#7 6 (×3) | Invossa 6 (×3) |
|---|---|---|---|---|---|---|
| Disorganization of | 1 | 1/15 | 1/18 | 7/18 | 9/18 | 6/18 |
| chondrocytes | 2 | 0/15 | 10/18 | 5/18 | 8/18 | 7/18 |
|  | 3 | 0/15 | 5/18 | 4/18 | 0/18 | 0/18 |
| Average pathology score |  | 0.07 | 2.00 | 1.61 | 1.39 | 1.11 |
| Standard Error |  | 0.07 | 0.23 | 0.24 | 0.15 | 0.20 |
| Exposure of | 1 | 0/15 | 7/18 | 6/18 | 4/18 | 6/18 |
| subchondral bone | 2 | 0/15 | 1/18 | 0/18 | 4/18 | 1/18 |
|  | 3 | 0/15 | 8/18 | 8/18 | 0/18 | 0/18 |
| Average pathology score |  | 0 | 1.83 | 1.67 | 0.67 | 0.44 |
| Standard Error |  | 0 | 0.29 | 0.30 | 0.21 | 0.15 |
| Cellular changes | 1 | 2/15 | 7/18 | 6/18 | 9/18 | 9/18 |
| of chondrocyte | 2 | 0/15 | 2/18 | 3/18 | 4/18 | 1/18 |
| H&E staining | 3 | 0/15 | 4/18 | 3/18 | 1/18 | 2/18 |
| Average pathology score |  | 0.13 | 1.28 | 1.17 | 1.11 | 0.94 |
| Standard Error |  | 0.09 | 0.27 | 0.26 | 0.17 | 0.20 |
| Degeneration/Necrosis | 1 | 0/15 | 3/18 | 2/18 | 5/18 | 6/18 |
|  | 2 | 0/15 | 4/18 | 8/18 | 5/18 | 4/18 |
|  | 3 | 0/15 | 11/18 | 8/18 | 5/18 | 0/18 |
| Average pathology score |  | 0 | 2.44 | 2.33 | 1.67 | 0.78 |
| Standard Error |  | 0 | 0.19 | 0.17 | 0.26 | 0.20 |
| H&E staining | 1 | 0/15 | 5/18 | 4/18 | 10/18 | 10/18 |
| Reduction of staining | 2 | 0/15 | 5/18 | 5/18 | 5/18 | 2/18 |
| in cartilage | 3 | 0/15 | 6/18 | 7/18 | 1/18 | 0/18 |
| Average pathology score |  | 0 | 1.83 | 1.94 | 1.28 | 0.78 |
| Standard Error |  | 0 | 0.23 | 0.23 | 0.17 | 0.14 |
| Total pathology score |  | 0.4 ± 0.32 | 15.44 ± 1.94 | 14.94 ± 1.88 | 10.94 ± 1.75 | 7.5 ± 1.57 |

Example 2: Analysis of Effect on Secretion of Anti-Inflammatory Cytokine by Treatment of Mixed Cell An effect on a cytokine expression profile of the synovial fluid in the articular cavity by treatment of mixed cells in an animal model was confirmed.

In order to confirm whether macrophages are induced at a cell site, it was confirmed that CD68 positive cells were present in the synovial membrane.

The paraffin-embedded synovial membrane was microsected with a thickness of 4 μm to prepare a tissue slide, and then immunohistochemical staining was performed by using CD68 antibodies (Novus, Co, USA).

Figure 7:
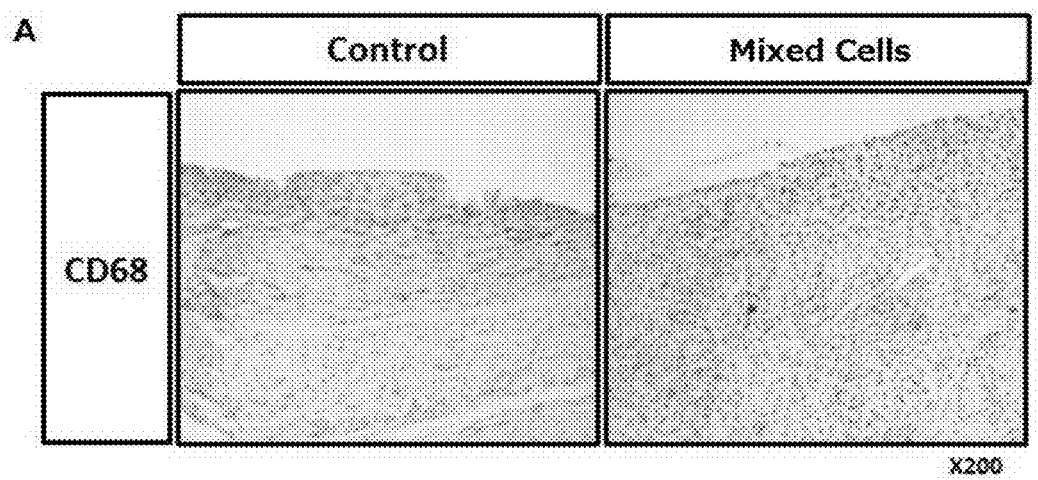
FIG. 7 illustrates the results for immunochemical staining of the synovial membrane with an antibody to CD68 which is a surface antigen of a macrophage and IL-10 antibody to confirm the macrophage status of the cell-treated articular cavity of a degenerative arthritis-induced animal.
Figure 7:
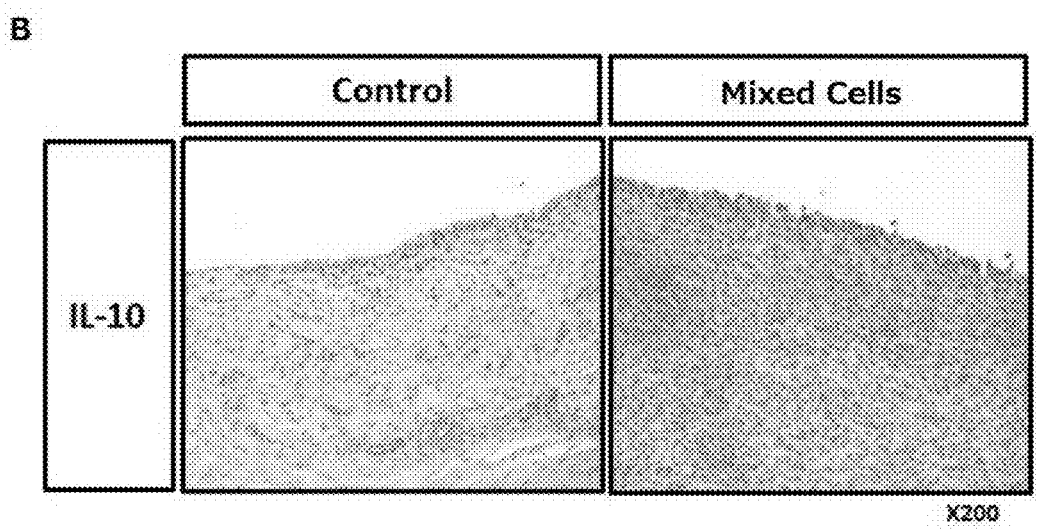

As a result, as illustrated in FIG. 7A, CD68-positive cells were significantly increased in the mixed cell-treated group.

IL-10 was known to exhibit the pain relief effect. An arthritis model was created based the above report and the mixed cell was treated, and then expression of IL-10 was confirmed. The expression of IL-10 was measured in the synovial lavage fluid of the arthritis-induced rat by using a cytokine magnetic bead panel 96-well plate assay (#RE-CYTMAG-65K, Milipore, USA).

Figure 6:
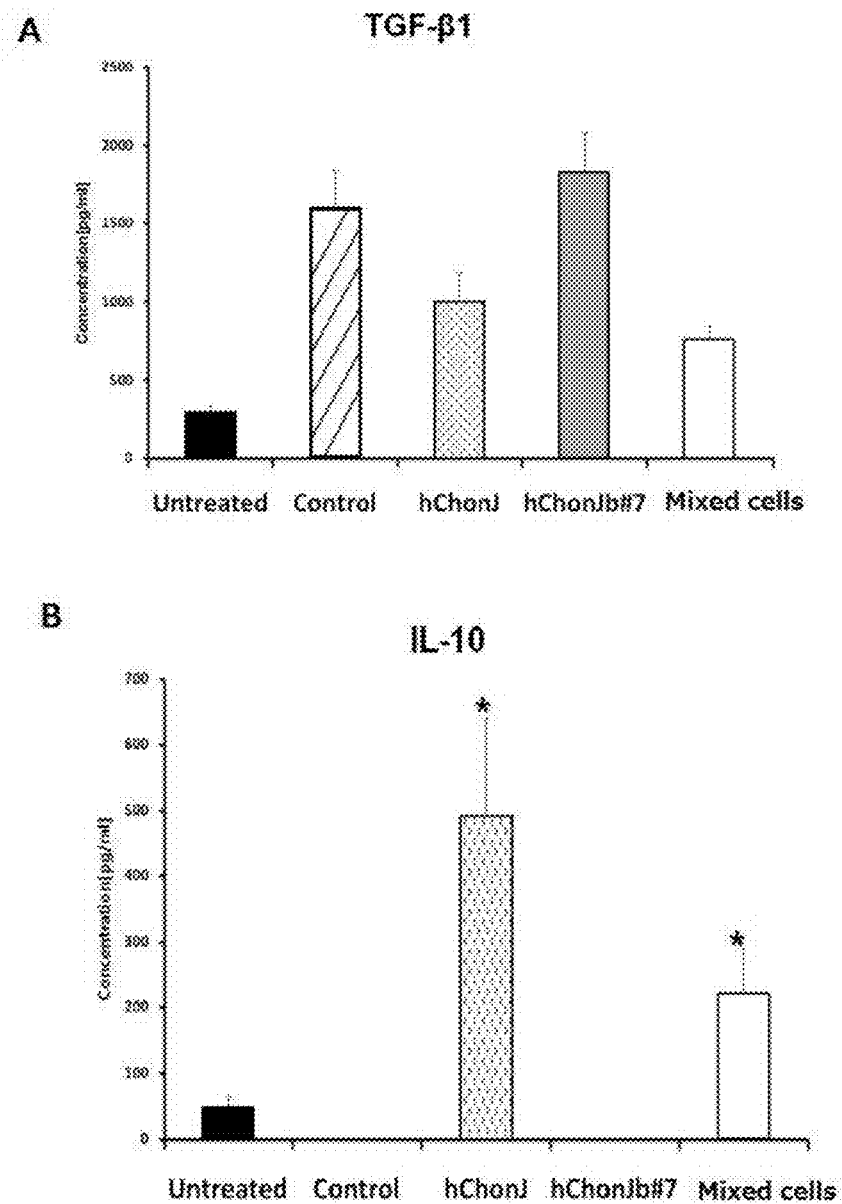
FIG. 6 illustrates the results for analysis on TGF-β1 and IL-10 expression levels in synovial lavage fluid in a degenerative arthritis-induced animal model.

As a result, as illustrated in FIG. 6B, in the mixed cell-treated group and the hChonJ-treated group, it was confirmed that the expression of IL-10 was increased. From the histological analysis result, it was confirmed that IL-10-positive cells were increased in the mixed cell-treated group. These results indicate that the treatment of the mixed cell in the arthritic knee joints induces IL-10 which is an anti-inflammatory cytokine.

Example 3: Confirmation of Induction of M2 Type Macrophage-Rich Environment by Mixed Cell There are two different types of macrophages. The M1 type macrophages are responsible for acute inflammation to secrete high levels of inflammatory cytokines such as IL-12 and TNF-α, and the M2 macrophages play an important role in wound healing and anti-inflammatory regulatory functions.

In Example 2, the high level of IL-10 expression was confirmed in the mixed cell-treated group, and as a result, in order to confirm whether the mixed cell induces the macrophages in the knee of the arthritis-induced animal, in the synovial membrane of the animal model, the expression of CD86 as a marker of the M1 macrophage and the expression of arginase 1 as a marker of the M2 macrophage were confirmed.

To this end, the paraffin-embedded synovial membrane was immuno-stained by using a CD86 antibody (AbD serotec, NC, USA) and a mouse arginase 1 antibody (BD Bioscience, USA).

As a result, as illustrated in FIGS. 8A through 8C, the expression of CD86 had no difference in the control and the mixed cell-treated group, but arginase 1 was significantly high in the mixed cell-treated group. It is shown that the mixed cells induce the M2 macrophages.

Example 4: Confirmation of Induction of M2 Macrophage-Rich Environment by Mixed Cell: RNA In order to confirm the induction of the M2 macrophages confirmed in Example 3 in the gene expression level, the total RNA was isolated from the synovial membrane of the animals and the expression of genes related with the M1 and M2 macrophages was confirmed.

The RNA in the synovial membrane was isolated by using a RNeasy Lipid Tissue Mini kit (QIAGEN, USA) and cDNA was synthesized from the isolated RNA by using a Super-Script™ III First-Strand Synthesis System (Invitrogen, USA).

Thereafter, real-time PCR was performed by using ABI7900 equipment. A PCR reaction mixture used 1 μL cDNA, 0.2 μM of each primer, and 10 μL SYBR Premix Ex Taq (TAKARA, Japan) at a total of 50 μL, and a reaction condition was 10 seconds at 95' C. and 30 seconds at 60° C. and a total of 40 cycles were performed. A gene expression level was confirmed by comparing an expression level of a β-actin gene by using a 2-ΔΔCt method and the used qRT-PCR primers were listed in Table 3

TABLE 3

Primer sequences used for qRT-PCR

| Gene | Forward primer | Reverse primer |
|---|---|---|
| CD80 | TGCTGGTTGGTCTTTTCCA | TGACTGCTCTTCAGAACAAAA |
| CD86 | TCCTCCAGCAGTGGGAAACATTTGTAGGTTTCGGGTATCCTTGC | |
| CD163 | CTCAGCGTCTCTGCTGTCACGGCCAGTCTCAGTTCCTTCTT | |
| Arg1 | TTGATGTTGATGGACTGGACTCTCTGGCTTATGATTACCTTC | |
| IL-1β | TCCAGGATGAGGACCCAAGCTCGTCATCATCCCACGAGTCA | |
| TNFα | ACTGAACTTCGGGGTGATTGGCTTGGTGGTTTGCTACGAC | |
| IL-10 | CAAGGCAGTGGAGCAGGTGACCGGGTGGTTCAATTTTTCATT | |
| Hmox-1 | AGAGTTTCCGCCTCCAACCACGGGACTGGGCTAGTTCAGG | |
| IL10Ra | CTGGTCACCCTGCCATTGATAGGCATGGCCAAAATACAAAGAAAC | |
| CD68 | ACTGGGGCTCTTGGAAACTACCTTGGTTTTGTTCGGGTTCA | |
| β-actin | AGTTCGCCATGGATGACGATAAGCCGGCCTTGCACAT | |

Figure 9:
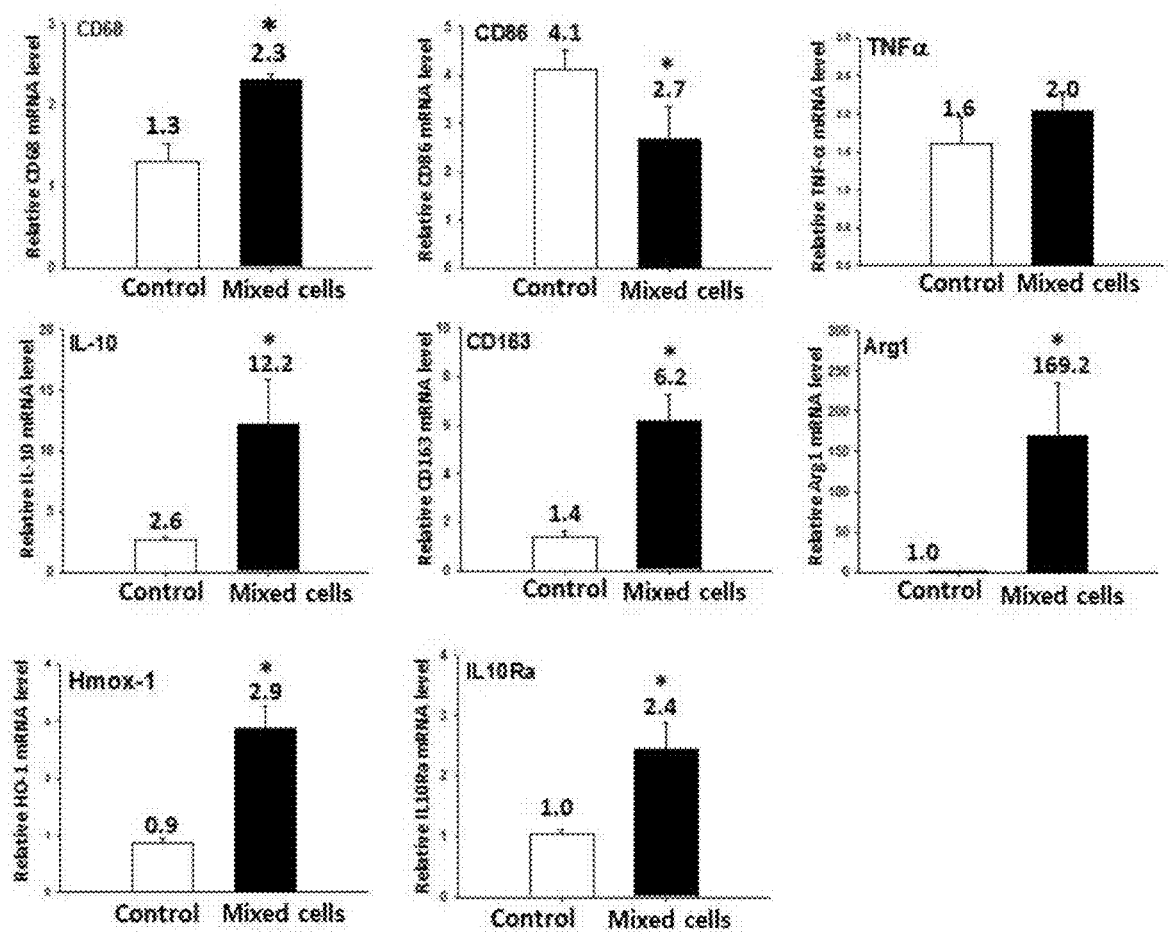
FIG. 9 illustrates the results for qRT-PCR of the gene expression profile in the synovial membrane.

Primer sequences for target genes for qRT-PCR of rat genes. CD = Cluster of Differentiation, Arg = Arginase, IL = Interleukin, TNFα = Tumor necrosis factors alpha, Hmox = Heme oxygenase A macrophage related gene expression profile is illustrated in FIG. 9. The expression of CD68 was high in the mixed cell-treated group. TNF-α had no difference between the control and the mixed cell-treated group IL-10 as an anti-inflammatory cytokine was very highly expressed in the mixed cell-treated group.

Figure 10:
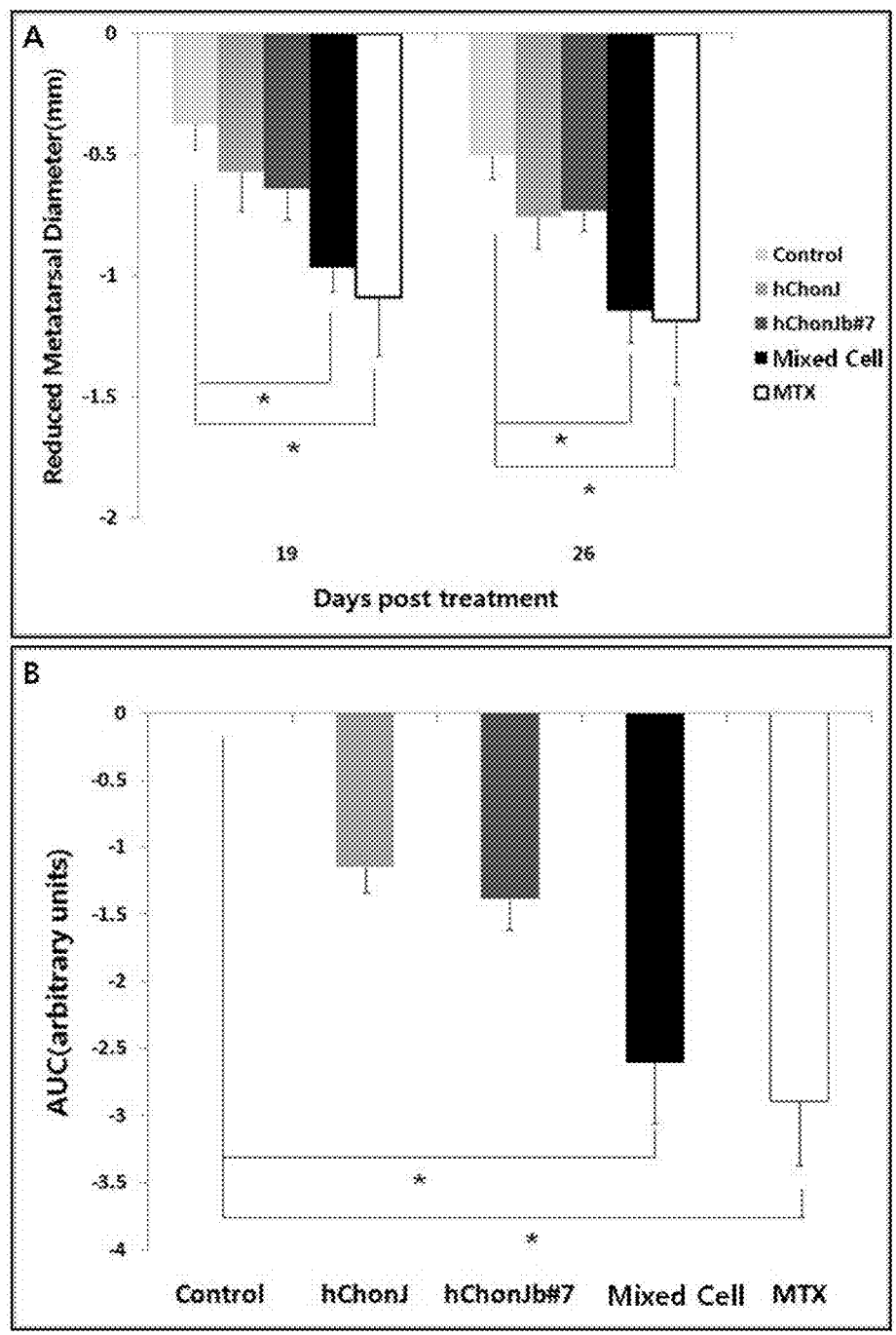
FIG. 10 is a graph illustrating the measurement results for edema reduction in the metatarsal region on the 19th day and 26th day after treatment of a mixed cell to a rheumatoid arthritis-induced animal model.

In order to confirm whether an increase in mRNA expression of IL-10 causes protein expression, a multiple cytokine assay in the synovial membrane was performed. As a result, as illustrated in FIGS. 10A and 10B, it was confirmed that in the mixed cell-treated group, a level of the IL-10 protein was rapidly increased. It was confirmed that the mRNA levels of IL-10RA (interleukin 10 receptor alpha subunit) and Hmox1 (heme oxygenase 1) which were additional macrophage markers were significantly increased.

When summarizing the results, in the case of administering the mixed cell in the arthritis model, it can be seen that induction of the M2 macrophages is increased.

Example 5: Confirmation of Efficacy of Mixed Cell in Rheumatoid Arthritis Animal Model 5-1: Preparation of Rheumatoid Arthritis Animal Model In a preparation of a rheumatoid arthritis-induced animal model, a 7-week-old female rat (160 to 180 g Lewis, Central laboratory animals, Japan) was used. The animal experiment was conducted after approval of the Kolon Life Science (Korea) Institutional Animal Care and Use Committee (IACUC No. KLS IACUC 2015-07).

In order to induce rheumatoid arthritis, 50 μl of a CFA (Complete Freud's Adjuvant, manufacturer: Chondrex, Inc.) solution having a concentration of 5 mg/mL was treated to the subcutaneous sole of a rat by using a 31 G syringe. After 3 weeks, induction of arthritis was confirmed by measuring the size of the metatarsal edema using calipers, and thereafter, when the edema was most severely induced, a test material was treated to the Lewis-rat left knee articular cavity 5-2. Treatment of Test Material to Animal Model Rheumatoid arthritis-induced rats were set to 6 rats per group, and after 3 weeks of CFA treatment, mixed cells {(1.2×10$^6$ cells: hChonJ (9×10$^5$ cells)+hChonJb#7 (3.0×10$^5$ cells)}, hChonJ (9×10$^5$ cells), hChonJb#7 (3.0×10$^5$ cells), and a negative control (CS-10) were treated to the left knee articular cavity. In the case of a positive control, 0.4 mg/kg of MTX (Methotrexate) was orally treated once a week. The metatarsal diameter and the body weight were measured once per three days.

In Table 4, a treatment condition for each experimental group was illustrated.

TABLE 4 treatment condition for each experimental group

| experimental group | | Cell/50 μl* | Number of Animal | Dosing Schedule | Method of Treatment |
|---|---|---|---|---|---|
| AIA | Negative Control Group | CS-10 | 6 | Single after 3 weeks inducing AIA | administration to the articular cavity |
| | hChonJ | 9 × 10$^5$ | 6 | | |
| | hChonJb#7 | 3 × 10$^5$ | 6 | | |
| | Mixed cell group | 1.2 × 10$^6$ | 6 | | |
| | MTX | 0.1 mg/kg | 6 | Once a week (21 d) | Oral treatment |

Treatment Condition for Each Experimental Group 5-3: Effect of Mixed Cell in Rheumatoid Arthritis Animal Model The test material was treated to the arthritis model and the size of the metatarsal edema was measured by a caliper, and the result was illustrated in FIGS. 10A and 10B. After treatment of the control (CS-10), hChonJ, hChonJb#7, mixed cell, and MTX (Methotrexate), the decrease in the size of the edema was measured on the 19th day and the 26th day, and as a result, in the mixed cell-treated group and the MTX-treated group, the decrease was statistically and significantly shown as compared with the control.

5-4: Analysis of Cytokine Secretion Profile by Treatment of Mixed Cell

Figure 11:
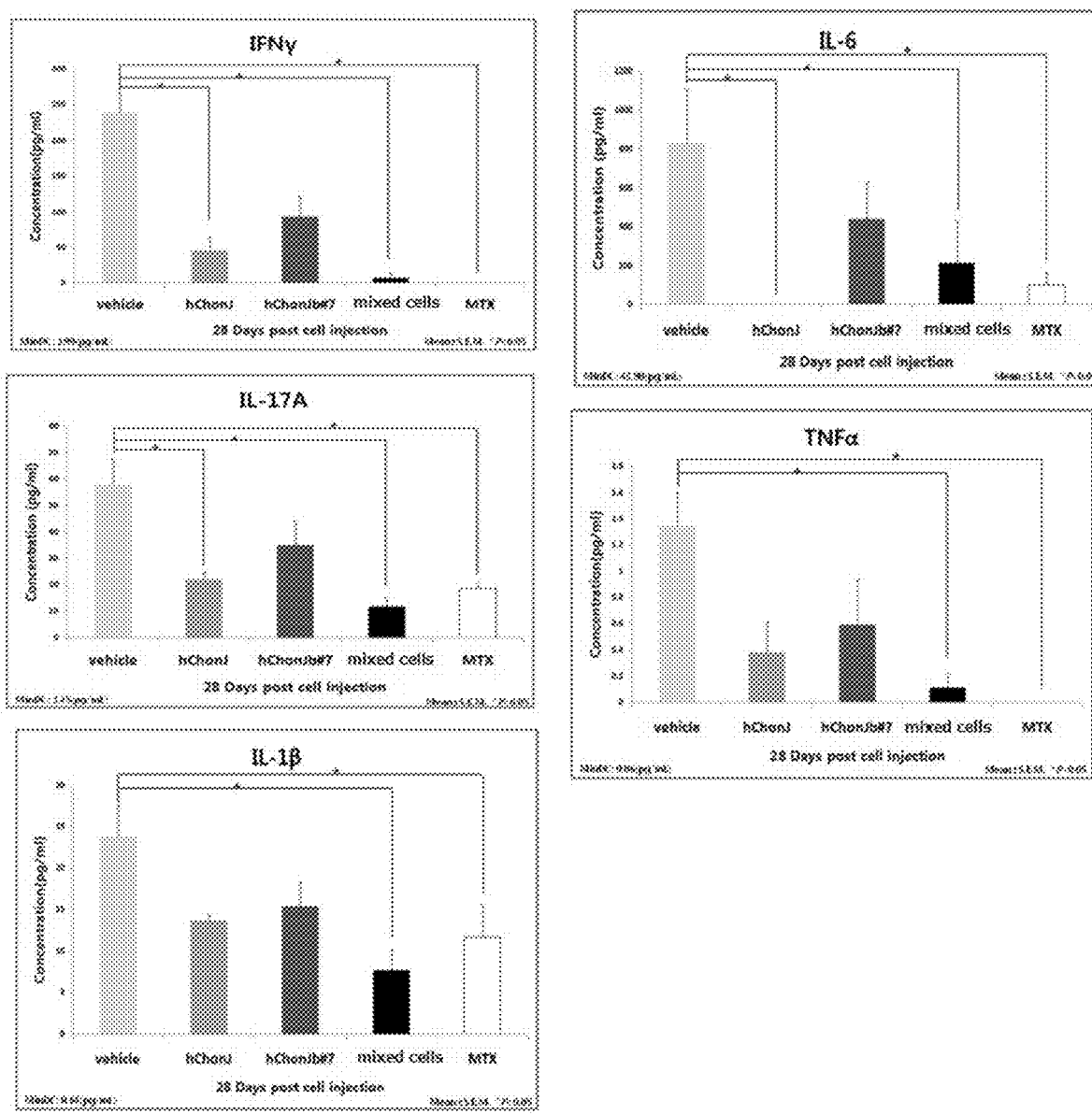
FIG. 11 illustrates the results for a change in cytokine measured by harvesting the synovial lavage fluid from the articular cavity on the 28th day after treatment of a mixed cell to a rheumatoid arthritis-induced animal model.

A sample was treated to the arthritis model, the synovial lavage fluid was harvested from the left knee articular cavity of the experimental animal rat on the 28th day, and the cytokines were analyzed, and the result was illustrated in FIG. 11. The synovial lavage fluid was collected from the rat articular cavity by administering 50 μL of a saline solution for injection by a 31 G insulin syringe and then immediately collecting the solution while the syringe pierced. As the cytokines, IFN-γ, IL-6, IL-17, IL-1β and TNF-α were analyzed and the analysis was performed by using Rat Cytokine/Chemokine multiplex (RECYTMAG-65K, Millipore). IFN-γ, IL-6, IL-17, IL-10 and TNF-α, which were Pro-inflammatory cytokine items inducing and promoting an inflammatory response, were analyzed and as a result, in the mixed cell-treated group and the MTX (Methotrexate)-treated group, the cytokines were statistically and significantly decreased as compared with the control.

The mixed cell composition of the present invention can improve symptoms of inflammatory diseases including rheumatoid arthritis and suppress a hyperimmune response by cell therapy without adverse effects from the other types of conventional drug therapy.

Although the specific part of the present invention has been described in detail, it is obvious to those expert in the field that such a specific description is just a preferred embodiment and the scope of the present invention is not limited. Thus, the substantial scope of the present invention will be defined by the appended claims and equivalents thereof.

What is claimed is:

1. A method of treating rheumatoid arthritis, the method comprising: administering directly to an articular cavity of a subject a composition comprising (i) a chondrocyte; and (ii) a cell into which a gene encoding TGF-β (transforming growth factor-beta) is introduced, wherein the cell in (ii) is hChonJb#7, wherein the administration of the composition has an effect of inhibiting expression of IL-6, IL-17A, IL-1β, and TNF-α in a synovial lavage fluid in the articular cavity of the subject.

2. The method according to claim 1, wherein a ratio of (i) the chondrocyte; and (ii) hChonJb#7 ranges from 1:1 to 100:1.

3. The method according to claim 2, wherein the ratio of (i) the chondrocyte; and (ii) hChonJb#7 ranges from 1:1 to 3:1.

4. A method of treating rheumatoid arthritis, the administering, directly to an articular cavity of a subject via an intra-articular injection a composition comprising (i) a chondrocyte; and (ii) hChonJb#7, wherein the administration of the composition has an effect of inhibiting expression of IL-6, IL-17A, IL-1β, and TNF-α in a synovial lavage fluid in the articular cavity of the subject.

* * * * *